United States Patent
Baram et al.

(10) Patent No.: US 10,973,461 B2
(45) Date of Patent: Apr. 13, 2021

(54) MAPPING OF INTRA-BODY CAVITY USING A DISTRIBUTED ULTRASOUND ARRAY ON BASKET CATHETER

(71) Applicant: Biosense Webster (Israel) Ltd., Yokneam (IL)

(72) Inventors: Alon Baram, Yokneam Ilit (IL); Meir Bar-Tal, Haifa (IL); Alona Sigal, Beit Hananya (IL)

(73) Assignee: Biosense Webster (Israel) Ltd., Yokneam (IL)

(*) Notice: Subject to any disclaimer, the term of this patent is extended or adjusted under 35 U.S.C. 154(b) by 345 days.

(21) Appl. No.: 15/866,784

(22) Filed: Jan. 10, 2018

(65) Prior Publication Data
US 2019/0209089 A1 Jul. 11, 2019

(51) Int. Cl.
| | |
|---|---|
| *A61B 5/00* | (2006.01) |
| *A61B 8/12* | (2006.01) |
| *A61B 8/08* | (2006.01) |
| *A61B 8/00* | (2006.01) |
| *G01S 15/89* | (2006.01) |

(Continued)

(52) U.S. Cl.
CPC ............ *A61B 5/6858* (2013.01); *A61B 5/061* (2013.01); *A61B 5/1076* (2013.01); *A61B 8/085* (2013.01); *A61B 8/0883* (2013.01); *A61B 8/12* (2013.01); *A61B 8/445* (2013.01); *A61B 8/5207* (2013.01); *A61B 8/54* (2013.01); *G01S 7/52028* (2013.01); *G01S 15/8915* (2013.01); *G01S 15/8929* (2013.01); *A61B 5/042* (2013.01); *A61B 5/6859* (2013.01); *A61B 8/4483* (2013.01);

(Continued)

(58) Field of Classification Search
None
See application file for complete search history.

(56) References Cited

U.S. PATENT DOCUMENTS

| | | | |
|---|---|---|---|
| 5,005,418 A | * | 4/1991 | Anderson ............. G01S 7/6245 73/625 |
| 5,027,658 A | | 7/1991 | Anderson |

(Continued)

OTHER PUBLICATIONS

Extended European Search Report dated Jun. 12, 2019 for the European Patent Application No. 19150987.6.

(Continued)

*Primary Examiner* — Katherine L Fernandez
(74) *Attorney, Agent, or Firm* — Volpe Koenig

(57) ABSTRACT

A medical system includes a shaft, multiple ultrasound transducers and a processor. The shaft is configured for insertion into an intra-body cavity of a patient. The multiple ultrasound transducers, which are distributed over splines that form a basket catheter at a distal end of the shaft, are configured to transmit ultrasonic signals in the intra-body cavity and to receive echo signals in response to the ultrasonic signals. The processor is configured to calculate a surface of the intra-body cavity by processing the echo signals using an ellipsoidal back-projection method, which reconstructs ultrasound-wave reflecting surfaces by performing at least one of applying back-projection summation over sub-sets of scattered echo signals distributed over respective sub-sets of constructed ellipsoids and applying a non-linear minimum operator over each of the sub-sets of distributed echo signals to generate a respective minimum value for each sub-set.

16 Claims, 3 Drawing Sheets

(51) Int. Cl.
*G01S 7/52* (2006.01)
*A61B 5/06* (2006.01)
*A61B 5/107* (2006.01)
*A61B 5/042* (2006.01)
*G06T 19/00* (2011.01)

(52) U.S. Cl.
CPC ............... *A61B 8/461* (2013.01); *A61B 8/48* (2013.01); *G06T 19/006* (2013.01)

(56) References Cited

U.S. PATENT DOCUMENTS

| | | | |
|---|---|---|---|
| 5,235,857 | A | 8/1993 | Anderson |
| 5,345,940 | A | 9/1994 | Seward et al. |
| 5,713,363 | A | 2/1998 | Seward et al. |
| 6,277,077 | B1 | 8/2001 | Brisken et al. |
| 6,716,166 | B2 | 4/2004 | Govari |
| 6,895,267 | B2 | 5/2005 | Panescu et al. |
| 7,610,078 | B2 | 10/2009 | Willis |
| 8,211,019 | B2 | 7/2012 | Sumi |
| 8,333,705 | B2 | 12/2012 | Hauck |
| 9,757,044 | B2 | 9/2017 | Scharf et al. |
| 2003/0072478 | A1* | 4/2003 | Claus .................... G06T 11/006 382/131 |
| 2011/0118590 | A1 | 5/2011 | Zhang |
| 2013/0116561 | A1* | 5/2013 | Rothberg ................. A61N 7/00 600/438 |
| 2014/0121470 | A1 | 5/2014 | Scharf et al. |
| 2015/0223757 | A1 | 8/2015 | Werneth et al. |

OTHER PUBLICATIONS

Anderson, "3D ellipsoidal backprojection images from large arrays. II," IEEE 1992 Ultrasonics Symposium Proceedings, Tucson, AZ, USA, pp. 1223-1226 vol. 2 (1992).

* cited by examiner

MAPPING OF INTRA-BODY CAVITY USING A DISTRIBUTED ULTRASOUND ARRAY ON BASKET CATHETER

FIELD OF THE INVENTION

The present invention relates generally to invasive medical instruments, and particularly to intra-body medical probes employing ultrasound.

BACKGROUND OF THE INVENTION

Methods of ultrasound spatial mapping and image-reconstruction of intra-body cavities, such as cardiac chambers, are often employed in medical applications. For example, U.S. Patent Application Publication 2015/0223757 describes systems, devices and methods for treating and/or diagnosing a heart arrhythmia, such as atrial fibrillation. Specifically, the invention provides a system including a diagnostic catheter and an ablation catheter. The diagnostic catheter includes a shaft, multiple dipole mapping electrodes and multiple ultrasound transducers arranged in a basket geometry. The ablation catheter is received by sliding the diagnostic catheter shaft.

As another example, U.S. Pat. No. 5,235,857 describes a real time 3D medical ultrasound imaging machine. Large extended transmitters are used with a great range of different pulse types, giving improved signal to noise ratio. The imaging machine can use small point like transmitters, one or more annular array transmitters, large curved transmitters or a large flat transmitter. Echoes are received by a sparse array of receiver elements. Image reconstruction is done by filtered ellipsoidal back-projections. The imaging machine additionally promises higher resolution, greater sensitivity 2D real time images displayed simultaneously with the real time 3D image.

A conference paper by Anderson, entitled "3D ellipsoidal back projection images from large arrays. II," Proceedings of the IEEE Ultrasonics Symposium, 1992, describes ellipsoidal back projection imaging that allows 3D ultrasonic images to be obtained in real time, i.e., at frame/s. In doing this, it overcomes a fundamental limitation of conventional focused beam imaging. High-quality ellipsoidal backpropagation images of a point are shown, wherein transmitter and receiver arrays of up to 512 elements are used. A method of synthesizing multiple transmitters using a defocused annular array is described.

U.S. Pat. No. 6,716,166 describes apparatus for mapping a surface of a cavity within a body of a subject using an elongate probe, having a longitudinal axis and including a distal portion adapted for insertion into the cavity. A plurality of acoustic transducers is distributed along the longitudinal axis over the distal portion of the probe, which transducers are adapted to be actuated individually to emit acoustic waves while the probe is in the cavity, and are further adapted to receive the acoustic waves after reflection of the waves from the surface of the cavity and to generate, responsive to the received waves, electrical signals indicative of times of flight of the waves.

U.S. Pat. No. 7,610,078 describes methods and systems for graphically creating a representation of an anatomical structure, such as a heart. The distal end of an elongated probe is moved within the anatomical structure, and geometric shapes are defined within a coordinate system. By defining geometric shapes, such as spheres or circles, as the distal probe end is moved within the anatomical structure such as a heart, the cavity within the anatomical structure can be represented. A representation of at least a portion of the anatomical structure can be graphically generated based on the geometric shapes, e.g., by determining a union of the geometric shapes and conforming the graphical representation around the union of the shapes.

U.S. Pat. No. 9,757,044 describes devices, systems, and methods for determining the dipole densities on heart walls. In particular, a triangularization of the heart wall is performed in which the dipole density of each of multiple regions correlate to the potential measured at various located within the associated cardiac chamber. To create a database of dipole densities, mapping information recorded by multiple electrodes located on one or more catheters and anatomical information is used. Additionally, one or more ultrasound elements are provided, such as on a clamp assembly or integral to a mapping electrode, to produce real time images of device components and surrounding structures. In an embodiment, a basket construction is provided that comprises multiple support arms which include one or more electrodes and one or more ultrasound elements.

SUMMARY OF THE INVENTION

An embodiment of the present invention provides a medical system including a shaft, multiple ultrasound transducers and a processor. The shaft is configured for insertion into an intra-body cavity of a patient. The multiple ultrasound transducers, which are distributed over splines that form a basket catheter at a distal end of the shaft, are configured to transmit ultrasonic signals in the intra-body cavity and to receive echo signals in response to the ultrasonic signals. The processor is configured to calculate a surface of the intra-body cavity by processing the echo signals using an ellipsoidal back-projection method, which reconstructs ultrasound-wave reflecting surfaces by performing at least one of applying back-projection summation over sub-sets of scattered echo signals distributed over respective sub-sets of constructed ellipsoids and applying a non-linear minimum operator over each of the sub-sets of distributed echo signals to generate a respective minimum value for each sub-set.

In some embodiments, the processor is configured to present to a user a diagram of the calculated surface of the intra-body cavity. In some embodiments, the intra-body cavity comprises a cardiac chamber.

There is additionally provided, in accordance with an embodiment of the present invention, a method including inserting a shaft into an intra-body cavity of a patient. Ultrasonic signals are transmitted in the intra-body cavity, and echo signals are received in response to the ultrasonic signals, by multiple ultrasound transducers which are distributed over splines that form a basket catheter at a distal end of the shaft. A surface of the intra-body cavity is calculated by processing the echo signals using an ellipsoidal back-projection method, which reconstructs ultrasound wave reflecting surfaces by performing at least one of applying back-projection summation over sub-sets of scattered echo signals distributed over respective sub-sets of constructed ellipsoids and applying a non-linear minimum operator over each of the sub-sets of distributed echo signals to generate a respective minimum value for each sub-set.

The present invention will be more fully understood from the following detailed description of the embodiments thereof, taken together with the drawings in which:

DETAILED DESCRIPTION OF EMBODIMENTS

Overview

Figure 1:
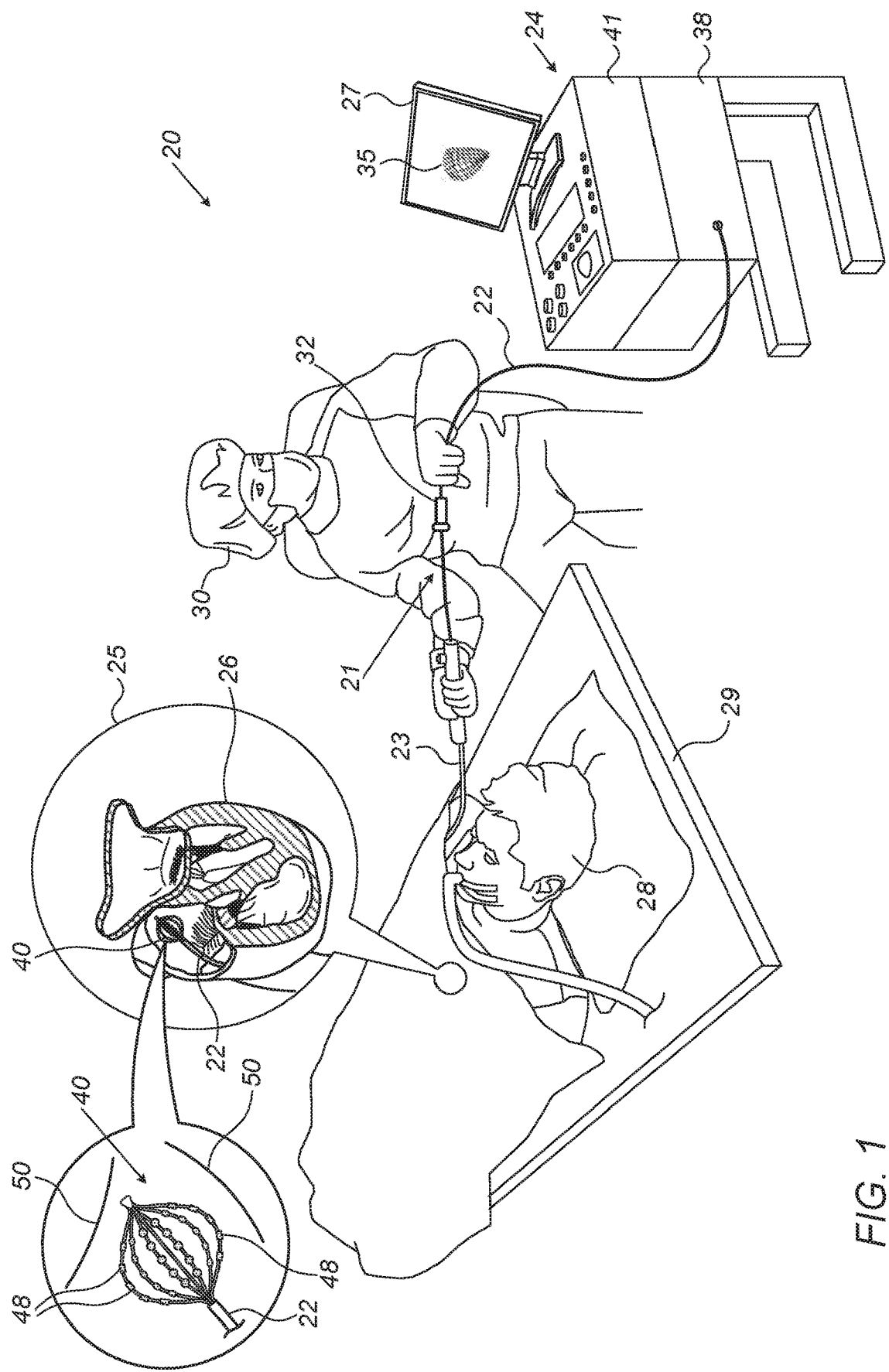
FIG. 1 is a schematic, pictorial illustration of a catheter-based cardiac mapping system comprising an ultrasound basket catheter, in accordance with an embodiment of the present invention.

Embodiments of the present invention that are described herein provide systems and methods that produce a spatial map of an intra-body cavity, such as a cardiac chamber, with enhanced contrast, while employing fast acquisition and reconstruction schemes. In some embodiments, an ultrasonic spatial mapping basket catheter is provided. The ultrasound basket catheter is capable of acquiring data to map an entire surface of a cardiac chamber from a single position in the cardiac chamber, e.g., without having to be rotated or moved across the chamber in the process. An improved reconstruction method is also provided, to be used with the ultrasound basket catheter, which enables reconstructing and presenting a spatial map that visualizes the enhanced contrast between the surface of a cardiac chamber and the blood within the chamber.

In some embodiments, the ultrasound basket catheter is fitted with multiple ultrasound transducers coupled to splines that form the basket shape. The transducers are distributed sparsely over the splines, and operate in Amplitude mode (A-mode) in order to generate and acquire one-dimensional echo signals. These echo signals are subsequently processed by a processor employing an ellipsoidal back-projection method so as to rapidly produce the required spatial map.

Briefly put, the ellipsoidal back-projection method, described in the Anderson article cited above, treats the following problem: 'assume to have finite number of transmitting/receiving ultrasound transducers where each transducer transmits an echo signal one at a time while all transducers receive scattered echo signals, what are the locations of scatters in the volume and what are the reflected amplitudes from the scatters?'

In the text hereinafter, the terms scattering and reflection are used interchangeably.

The method by Anderson solves the problem by first assigning to each scatter at a location X a scattered signal S(X) that is modeled by summing over all potentially contributing signals $S_k(X)$ detected at a given time by the receiving transducers. The partial signals $S_k(X)$ are signals defined by a triplet of coordinates of three objects in space: (source transducer location, scatter location, receiving transducer location). Such triplets uniquely define respective ellipsoids in space. One or more, enumerated K, ellipsoids may contribute to S(X). Thus, the ellipsoid back-projection model constructs the signal at X, as $S(X)=Sum\{S_k(X)\}$, k=1, 2, ... K. In the description hereinafter, a group of signals $\{S_k(X)\}$, is named 'sub-set of scattered signals.'

In the description above, all the K scatter ellipsoids that belong to a given sub-set are defined by (i) a pair of transducers, and (ii) a single point location X in the body where a single scattering occurs at. The back-projection of S(X), P(S(X)), performed for all coordinates X in a volume generates the required spatial map P(X), as described in detail below.

In an embodiment, a disclosed variant of the ellipsoidal back-projection method achieves higher contrast between the surface of the chamber and the blood within. To achieve the enhanced contrast, a processor applies a non-linear minimum filter over all sub-sets of scattered signals from all mapped locations in space. As a result, generally all resulting signals are attenuated by the operator, however the signal to noise ratio improves. In the description hereinafter, the term 'signal' means large partial echo amplitudes $S_k(X)$ that usually originate from interfaces. In the description hereinafter, the term 'noise' means small partial echo amplitudes, $S_k(X)$ signals that are erroneously attributed by the back-projection algorithm to scattering, e.g., from nonexistent scatters such as from part of a homogenous environment (e.g., blood pool).

As a result of the variant described above, the ultrasound-derived density of the blood inside a chamber of a heart receives a proper low value (as opposed to an artificially high value obtained by the original ellipsoidal back-projection method). As indicated above, the ultrasound-derived density of would be attenuated as well, but the overall signal to noise improve. Thus, the variant process described briefly above improves the contrast between chamber-surface and blood.

The accuracy of a spatial map of a cardiac chamber would benefit from faster acquisition and reconstruction times. In an embodiment, the disclosed method shortens calculation times by producing a synthetic spatial map, which is based on analyzing one-dimensional A-mode signals, rather than attempting to perform an unnecessary and computationally-demanding full image reconstruction.

The disclosed systems and methods, which combine (i) a basket ultrasound array that instantaneously acquires multiple ultrasound measurements and (ii) an improved reconstruction scheme, may be advantageous to the physician, who may receive more accurate spatial and functional maps of an intra-body cavity, such as a cardiac chamber. Hence, the disclosed system and method may enable the physician to perform efficient invasive diagnostics and possibly subsequent treatment sessions.

System Description

FIG. 1 is a schematic, pictorial illustration of a catheter-based cardiac mapping system 20 comprising an ultrasound basket catheter 40, in accordance with an embodiment of the present invention. System 20 comprises a catheter 21, having a shaft 22 that is navigated by a physician 30 into a heart 26 of a patient 28 lying on a table 29. In the pictured example, physician 30 inserts shaft 22 through a sheath 23, while manipulating the distal end of shaft 22 using a manipulator 32 near the proximal end of the catheter and/or deflection from the sheath 23. As shown in an inset 25, basket catheter 40 is fitted at the distal end of shaft 22. Basket catheter 40 is inserted through sheath 23 in a collapsed state and is then expanded within heart 26.

In an embodiment, basket catheter 40 is configured to perform spatial mapping of a cardiac chamber of heart 26 by transmitting echo signals and receiving echo signals that were reflected from cardiac chamber surfaces 50. An inset 45 shows basket catheter 40 in an enlarged view, inside a cardiac chamber of heart 26. As seen, basket catheter 40 comprises an array of ultrasound transducers 48 coupled onto splines that form the basket shape.

The proximal end of catheter 21 is connected to a console 24. Console 24 comprises a processor 41, typically a general-purpose computer, with suitable front end and interface circuits 38 for transmitting and receiving signals to and from catheter 21, as well as for controlling the other components of system 20. In some embodiments, processor 41 is further configured to receive multiple one-dimensional echo signals and to calculate from these signals a map of a surface of a cardiac chamber. In an embodiment, the surface of the surrounding anatomy is presented to physician 30 on a monitor 27, e.g., in a graphical form of a mesh diagram 35.

As noted above, processor 41 typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The example configuration shown in FIG. 1 is chosen purely for the sake of conceptual clarity. The disclosed techniques may similarly be applied using other system components and settings. Additionally, system 20 may comprise additional components, such as ones for electrophysiological mapping and/or ablation.

Although the pictured embodiment relates specifically to the use of an ultrasound basket catheter for cardiac mapping, the elements of system 20 and the methods described herein may alternatively be applied in ultrasound mapping using catheters having other multi-arm geometries.

Figure 2:
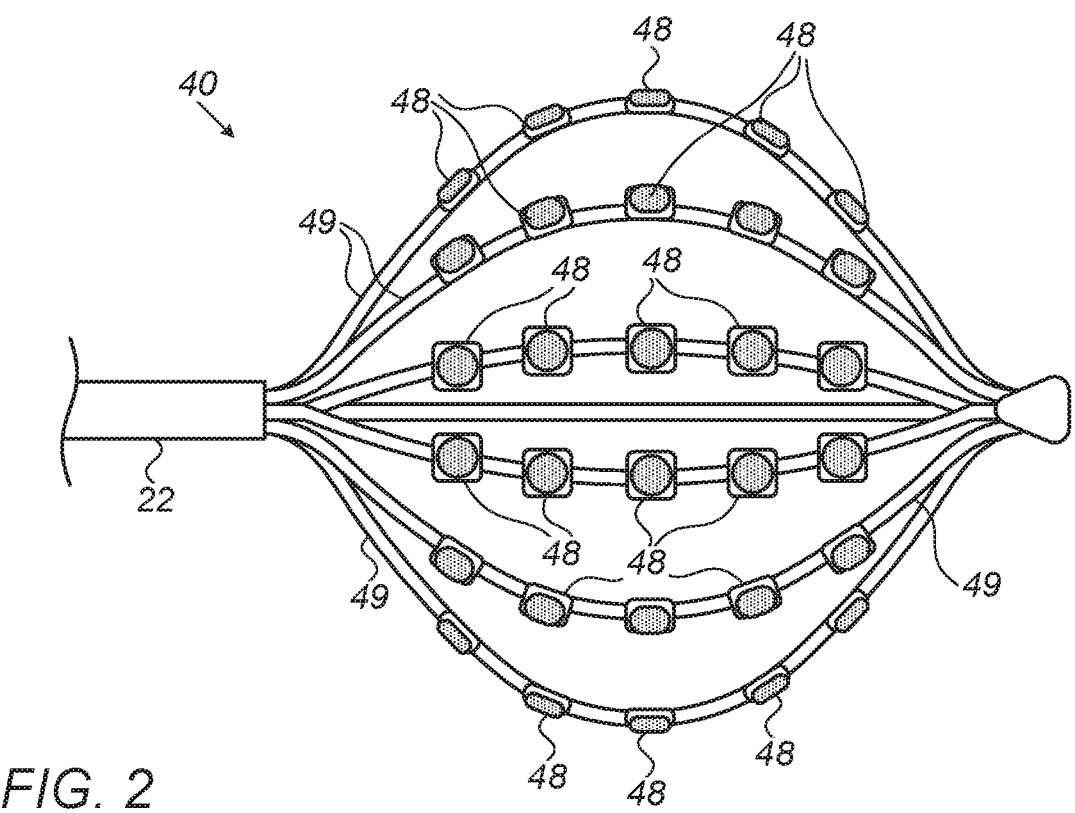
FIG. 2 is a schematic, pictorial illustration of a basket catheter fitted with ultrasound transducers, in accordance with an embodiment of the present invention.

Mapping of Intra-Body Cavity Using a Distributed Ultrasound Array on Basket Catheter FIG. 2 is a schematic, pictorial illustration of a basket catheter 40 fitted with ultrasound transducers 48, in accordance with an embodiment of the present invention. As seen, transducers 48 are coupled to splines 49 that form the basket. Transducers 48 are sparsely distributed (i.e., where a large gap exists between each two neighboring transducers, such that the majority of surface area of a basket surface defined splines 49 is vacant of transducers) approximately spherically beyond the distal end of shaft 22. The array of transducers 48 can achieve the required coverage and detail of features of a cardiac chamber despite being sparse because (a) each transducer has sufficiently large transmitting and receiving acceptance angle (b) the calculations are optimized to utilize sparse arrays, as explained below.

The example illustration shown in FIG. 2 is chosen purely for the sake of conceptual clarity. The number of transducers and their arrangement may vary. Additional elements. Such as electrodes, may be disposed over splines 49. Other catheter geometries may be used to carry transducers 48, for example such made of spiraling arms.

Figure 3:
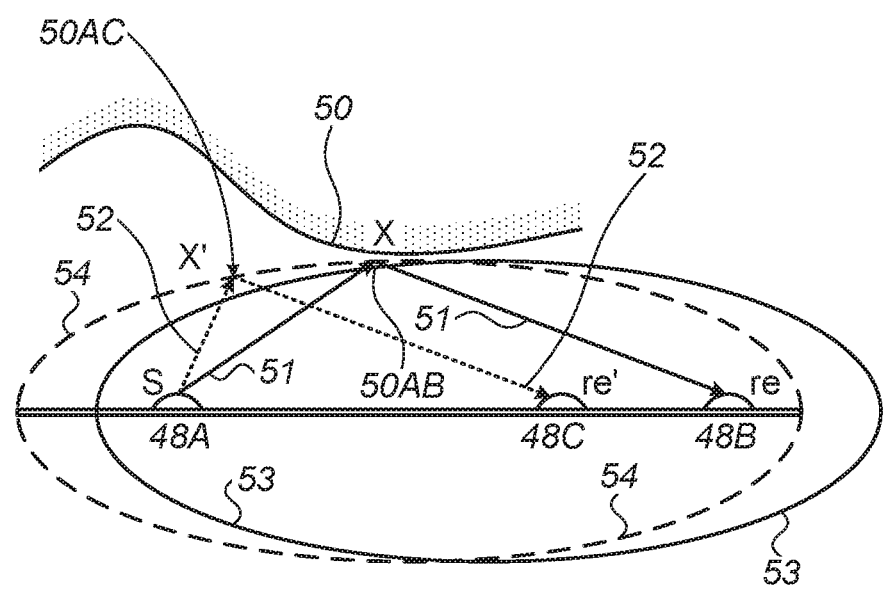
FIG. 3 is a schematic, pictorial illustration of an ellipsoidal back-projection scheme, in accordance with an embodiment of the present invention.

FIG. 3 is a schematic, pictorial illustration of an ellipsoidal back-projection scheme, in accordance with an embodiment of the present invention. In order to simplify the graphical presentation, and without loss of generality, FIG. 3 provides a two-dimensional elliptical illustration of the three-dimensional ellipsoidal back-projection model.

The model by Anderson assumes each transmitting transducer (exemplified by a transducer 48A in FIG. 3) that is located at a position $s \in R^3$ is a source of a spherical ultrasound pressure wave of the form $$P_S(r, t) = P_0 \frac{1}{4\pi r} \delta(r - ct),$$

where r is the distance from the transmitter at s and c is the velocity of sound in the medium and $P_0$ is the signal amplitude. The method examines what happens when a transmitter located at s transmits a pulse scattered by scatter (exemplified by 50AB in FIG. 3) located at X and received by a transducer (exemplified by 48B in FIG. 3) at re. The scattering element is considered as a secondary spherical wave source. Let $D(x,y)=\|x-y\|$ denote the Euclidian distance between positions x and y in $R^3$. The pressure pulse wave transmitted by a source at position s arrives at a scatter at position X after time $$t_1 = \frac{D(s, X)}{c}.$$

Then the pulse is scattered in all directions as $$P_1 \frac{1}{4\pi r} \delta(r - c(t - t_1)) = \widetilde{P_1} P_0 \frac{\delta(r - ct + D(s, X))}{16\pi^2 r D(s, X)},$$

where $P_1$ is the incoming pulse amplitude and after substitution $\widetilde{P_1}$ is the reflected proportion of energy which depends on reflective indices geometry and matter properties. r is the distance from the scatter to a receiver. The receiver located at re thus receives the following amplitude from the scatter:

$$\sigma(s, X, re) = \widetilde{P_1} P_0 \frac{\delta(ct - (D(s, X) + D(X, re))}{16\pi^2 D(X, re) D(s, X)} \propto S_k(X),$$

where $S_k(X)$ is the partial signal, and k denotes an index associated a certain transmitter-receiver pair. The signal is received at time $$t_{s,re} = \frac{(D(s, X) + D(X, re)}{c},$$

which is the travel time from the source to the scattering element and the receiver.

The triplet (s,X,re) defines an ellipsoid 53 in $R^3$ with major axis $c \cdot t_{s,re} = D(s,X) + D((X,re)$, where s and re lie on his axis and X is on the boundary. Any other scattering element on the boundary of this ellipsoid will have the same travel time $t_{s,re}$. In other words, the signal received at time $t_{s,re}$ when transmitted at t=0 is the integral over the contribution of all scattering elements that lie on the surface of ellipsoid 53. The acquired signal over time for a transmitter receiver pair at a time t as a surface integral over the induced ellipsoid E(s,X,t) is expressed as:

$$S(s, re, t) = \oint_{X \in E(s,X,t)} \sigma(s, X, re) dX = \oint_{X \in E(s,X,t)} \widetilde{P_1} P_0 \frac{\delta(ct - (D(s, X) + D(X, re))}{16\pi^2 D(X, re) D(s, X)} dX$$

The ellipsoidal back-projection operator is then defined as:

$$P(X) = \int\int\int_{s,re \in V} S(s, re, t) \delta\left(t - \frac{D(s, X) + D(X, re)}{c}\right),$$

which is a summation over of all possible receiver-transmitter transducer pairs in the volume at all times in which X contributes to the signal recorded in the receivers. i.e., X defines the ellipsoid among that triplet coordinates.

Note, in the absence of noise, for locations X where no true scatters exist P(X) should have zero value. This means that ideally, the described method should produce good tissue contrast resolution.

In some implementations use discrete space, time, signals, and number of transmitters/receivers. Sampling is made over a volume of space at some Cartesian grid uniformly. Time is taken at steps dt. The ultrasound array is assumed to include N transmitters/receivers. The discreet back-projection operator takes the form:

$$P'(X) = \sum_{s,re \in N, t} S\left(s, re, t\right) E\left(s, re, t = \left[\frac{D(s, X) + D(X, re)}{c \cdot dt}\right]dt\right)$$

The summation is done only for s, re and t, where $X \in E(s,X,t)$, a group denoted in the description as $\{X\}_K$, where K is the number of the ellipsoids belonging to that group. When there are enough transcoders in the array, the discrete operator should well-approximate the continuous one. When computing this operation for every voxel in a sampled grid, a spatial map P'(X), representing the distribution of scattering elements in the volume is received, such as a map of a cardiac chamber.

In practice, a source of spatial-noise exists in P'(X), due to a mechanism where any noise detected by a transducer, such as transducer 48C, can be fitted to respective echo trajectory 52 that erroneously trace the noise detected at transducer 48C as a true signal that originated from emitting transducer 48A. An ellipsoid 54, E(s,X'(50AC),re'), is constructed thus that is fully defined by pair transducers-pair (48A,48C) and a nonexistent-scatter 50AC located at X'. In the description hereinafter, an ellipsoid such as ellipsoid 54 may be described as 'noise-generated'. Additional steps described above lead to a non-zero valued P'(X').

The method by Anderson, thus may result in an over estimated ultrasound-derived density of locations such as 50AC (e.g., locations in the blood inside a cardiac chamber). Subsequently, locations like 50AC receive artificially high values on a spatial map, harming contrast resolution, and therefore the ability to resolve true-reflecting surfaces, such as tissue of a cardiac chamber.

The ellipsoidal back-projection method exemplified in FIG. 3 is partially based on U.S. Pat. No. 5,235,857, whose disclosures are incorporated herein by reference.

As noted above, possibly many more back-projection reconstructed ellipsoids belonging to the same sub-set (i.e., pass through a location X) being defined by other transducer-pairs. Such sub-set of ellipsoids (related to location X), which may contain K ellipsoids, is defined in the description hereinafter as $$\{X\}_K = \{(s,re,t) | X \in E(s,re,t)\}$$

where $\{X\}_K$ contain all ellipsoids constructed from an echo signal with assumed time of flight t, which is assumed to be traveling between a source transducer at position s, scattered at location $\{X\}$, and received (at another transducer at a position re.

As noted, all ellipsoids belonging to sub-set $\{X'\}_K$ are noise generated, as no reflections exist in reality from location X'. As indicated above, summing noises, such as a noise over ellipsoid sub-set $\{X'\}_K$ may damage the quality of a resulting spatial map.

In an embodiment, a method is provided for achieving enhanced contrast between blood filling a chamber and a surface of that chamber. This variant over the ellipsoidal back-projection method by Anderson uses the observation that for any location X in a volume, if there is one ellipsoid that is noise generated, then the location lies in free space and all other related ellipsoids are necessarily also noise generated.

Mathematically, a minimum non-linear operator F(X) is applied over each and any sub-set of scattered signals, $\{S_k(X)\}_K$, from each and any location X.

The minimum non-linear operator F(X) is applied by a processor in the following way: instead of the processor performing summations on over $\{S_k(X)\}_K$, the minimum non-linear operator is applied over $\{S_k(X)\}_K$, where $\{X\}_K = \{(s,re,t) | X \in E(s,re,t)\}$:

$$F(X) = \text{Min}\{\{S_k(X)\}_K\} = \text{Min}_{(s,re,t) | X \in E(s,re,t)} |S(s,re,t)|,$$

where S(s,re,t) denotes the acquired signal over time for a transmitter receiver pair at a time t associated with each of the ellipsoids that pass-through location X. Thus F(X) is the global minimum provided by the non-linear minimum filter for any location X.

Such minimum operation produces a very low value of noise, such as from 50AC at X', i.e., F(X') yields the lowest noise associated with location like location X', which would therefore not hurt tissue contrast resolution. As noted above, despite F attenuating also signals, such as from 50AB at X, the overhaul signal to noise improves by applying F.

In an embodiment, instead of using the absolute value we take the Hilbert transform of the signal which is a method of extracting the signal's envelope. The method by Anderson was suggesting using coherent summing with an anticipation that noise will cancel out. Coherent sum assumes exact phase difference (up to about ¼ wavelength) is known. In practice this is very difficult to ensure, since the basket is not rigid and the wavelength is less than 1 mm. Using the envelope signal (i.e., energy sums) has the advantage of losing the need for coherent summing making the algorithm more robust to location errors in array element positions. In an embodiment, an error of up to 2 mm in intra-transducer distances is acceptable.

In an embodiment, the present invention is realized by a 64 piezoelectric transducers array is mounted on 12 splines. The transducers have a resonance frequency of about 1.4 Mhz and the sampled voxel size is $1.4=^3$. The transducers are connected to an acquisition system capable of generating pulses and record a sweep of a transmission over all elements in real time. The calculations are performed with weighted directivity (by convolving the transmitted signal with transmitter and receiver transfer function in time, and using Huygens principle in space) and applying calculations performed on Hilbert transformed echo signals. Signals from voxel elements that are in the back side of a transmitting or receiving transducer (i.e., not in the half plane directed by their normal) are discarded. This is done to reduce noise coming from spline echo and other weak reflections. The above embodiments serve as an example.

The number and size of transducers, the resonance frequency and the voxel size may vary, among other parameters.

The example of signals shown in FIG. 3 is chosen purely for the sake of conceptual clarity. As noted above, it is to be understood that the enclosed graphical description is simplified only for the sake of clarity of the figures.

Figure 4:
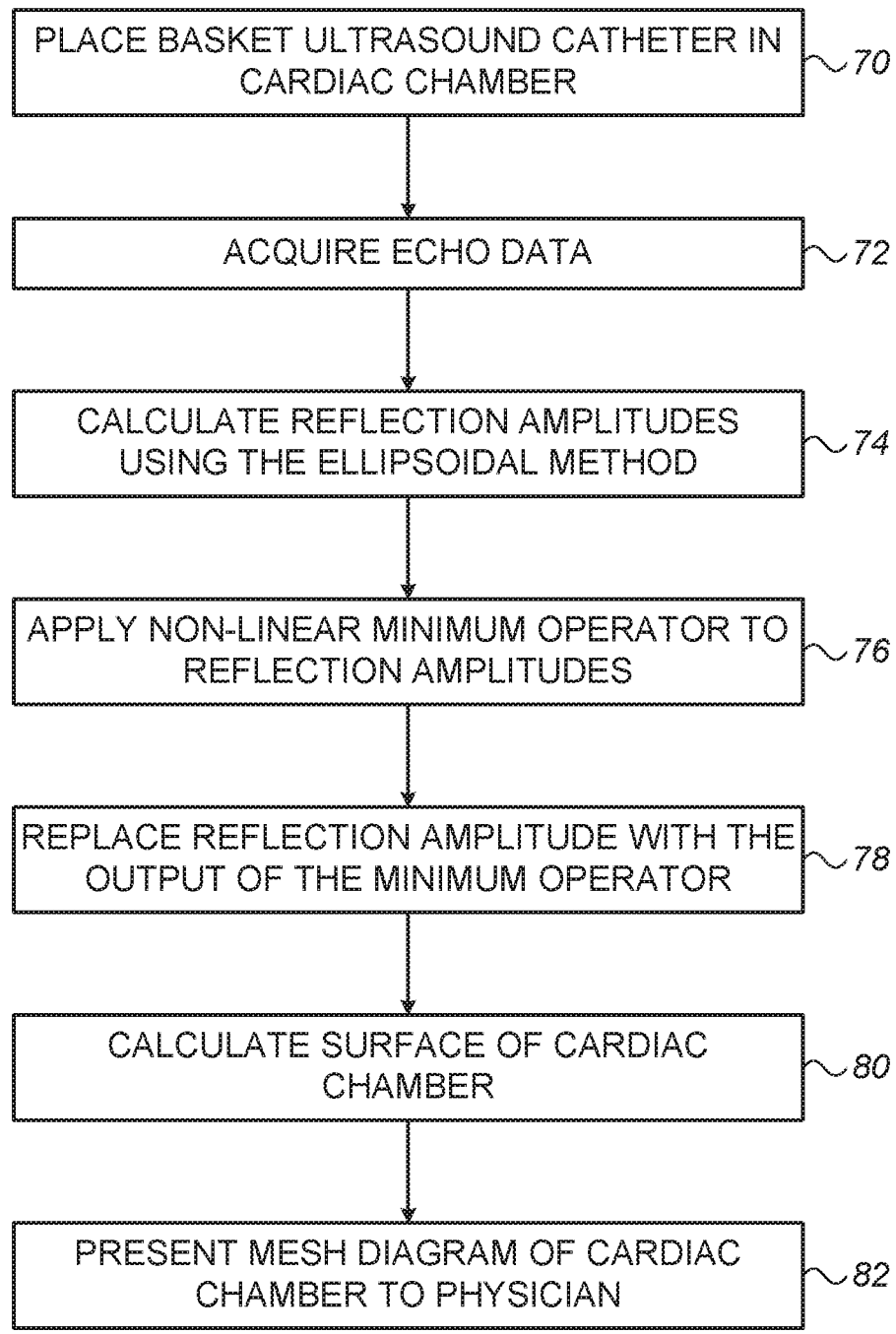
FIG. 4 is a flow-chart that schematically illustrates a method for mapping and presenting a cardiac chamber, in accordance with an embodiment of the present invention.

FIG. 4 is a flow-chart that schematically illustrates a method for mapping and presenting a cardiac chamber, in accordance with an embodiment of the present invention. The method begins by physician 30 inserting and placing an ultrasound basket catheter 40 into a cardiac chamber of heart 26, in a placement step 70. At an acquisition step 72, the array of transducers 48 transmit and receive echo signals, where resulted electrical signals are communicated by wiring running through shaft 22 to processor 41. At a calculation step 74, processor 41 calculates reflection amplitudes starting by fitting a sub-set of scatter ellipsoids to each received sub-set of distributed echo signals. Next, processor 41 applies a non-linear minimum operator over the sub-set of distributed echo signals, at a minimization step 76. As a result, the reflected amplitudes are replaced by the respective output value of the minimum operator (a non-negative minimal value), as explained above, at a replacement step 78. Finally, processor 41 sums over all signals so as to calculate anatomical surface 50 geometry of the cardiac chamber, at calculation step 80. A resulting diagram, such as mesh diagram 35 representing a surface of a cardiac chamber, is presented to physician 30 on display 27, at a presentation step 82.

The example flow chart shown in FIG. 4 is chosen purely for the sake of conceptual clarity. For example, additional calculation steps that take place are omitted for simplifying the description. Further diagnostic and treatment steps that may be included in the flow-chart, such as electrophysiological mapping and ablation, are also omitted from this description, to keep the flow chart concise.

Although the embodiments described herein mainly address ultrasound acquisition and reconstruction of cardiac anatomy, the methods and systems described herein can also be used in other applications, such as in gastroenterology and angioplasty.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical system for mapping a surface of a cardiac chamber, comprising:
   a shaft for insertion into the cardiac chamber;
   multiple ultrasound transducers, which are distributed over splines that form a basket catheter at a distal end of the shaft, and which are configured to transmit ultrasonic signals in the cardiac chamber and to receive one-dimensional Amplitude mode echo signals in response to the ultrasonic signals; and
   a processor configured to calculate the surface of the cardiac chamber by processing the one-dimensional Amplitude mode echo signals using an ellipsoidal back-projection method, which produces a synthetic spatial map of the cardiac chamber by performing the following:
      applying Hilbert transform to the one-dimensional Amplitude mode echo signals to obtain a plurality of scattered Hilbert transformed one-dimensional Amplitude mode echo signals;
      calculating reflection amplitudes of sub-sets of the plurality of scattered Hilbert transformed one-dimensional Amplitude mode echo signals distributed over respective sub-sets of constructed ellipsoids;
      applying a non-linear minimum operator over the sub-sets of the plurality of scattered Hilbert transformed one-dimensional Amplitude mode echo signals;
      producing the synthetic spatial map of the cardiac chamber by applying back-projection summation over the sub-sets of the plurality of scattered Hilbert transformed one-dimensional Amplitude mode echo signals in which each of the calculated reflection amplitudes are replaced with a respective output value of the non-linear minimum operator.

2. The medical system according to claim 1, wherein the processor is configured to present to a user the synthetic spatial map comprising a diagram of a calculated surface of the cardiac chamber.

3. The medical system according to claim 1, wherein upon replacing each of the calculated reflection amplitudes with the respective output value of the minimum operator, the processor is configured to produce a signal to noise ratio.

4. The medical system according to claim 3, wherein the signal to noise ratio comprises a ratio between echo signals reflected from the surface of the cardiac chamber and echo signals that are not reflected from the surface of the cardiac chamber.

5. The medical system according to claim 4, wherein the surface of the cardiac chamber comprises a tissue of the cardiac chamber.

6. The medical system according to claim 4, wherein the echo signals that are not reflected from the surface of the cardiac chamber comprise signals reflected from a blood pool of the cardiac chamber.

7. The medical system according to claim 1, wherein the synthetic spatial map comprises a mesh diagram of the surface of the cardiac chamber.

8. The medical system according to claim 1, wherein the system is configured to ablate a target on the surface of the cardiac chamber.

9. A method, comprising:
   providing a medical system for mapping a surface of a cardiac chamber;
   inserting a shaft into an cardiac chamber of a patient;
   transmitting ultrasonic signals in the cardiac chamber, and receiving one-dimensional Amplitude mode echo signals in response to the ultrasonic signals, by multiple ultrasound transducers which are distributed over splines that form a basket catheter at a distal end of the shaft; and
   calculating, in a processor, the surface of the cardiac chamber by processing the one-dimensional Amplitude mode echo signals using an ellipsoidal back-projection method, which produces a synthetic spatial map of the cardiac chamber by performing the following:

applying Hilbert transform to the one-dimensional Amplitude mode echo signals to obtain a plurality of scattered Hilbert transformed one-dimensional Amplitude mode echo signals;

calculating reflection amplitudes of sub-sets of the plurality of scattered Hilbert transformed one-dimensional Amplitude mode echo signals distributed over respective sub-sets of constructed ellipsoids;

applying a non-linear minimum operator over the sub-sets of the plurality of scattered Hilbert transformed one-dimensional Amplitude mode echo signals;

producing the synthetic spatial map of the cardiac chamber by applying back-projection summation over the sub-sets of the plurality of scattered Hilbert transformed one-dimensional Amplitude mode echo signals in which each of the calculated reflection amplitudes are replaced with a respective output value of the non-linear minimum operator.

10. The method according to claim 9, further comprising presenting to a user the synthetic spatial map comprising a diagram of a calculated surface of the cardiac chamber.

11. The method according to claim 9, further comprising upon replacing each of the calculated reflection amplitudes with the respective output value of the minimum operator:
producing a signal to noise ratio.

12. The method according to claim 11, wherein the signal to noise ratio comprises a ratio between echo signals reflected from the surface of the cardiac chamber and echo signals that are not reflected from the surface of the cardiac chamber.

13. The method according to claim 12, wherein the surface of the cardiac chamber comprises a tissue of the cardiac chamber.

14. The method according to claim 12, wherein the echo signals that are not reflected from the surface of the cardiac chamber comprise signals reflected from a blood pool of the cardiac chamber.

15. The method according to claim 9, wherein the synthetic spatial map comprises a mesh diagram of the surface of the cardiac chamber.

16. The method according to claim 9, further comprising:
ablating a target on the surface of the cardiac chamber.

* * * * *

UNITED STATES PATENT AND TRADEMARK OFFICE
CERTIFICATE OF CORRECTION

PATENT NO. : 10,973,461 B2
APPLICATION NO. : 15/866784
DATED : April 13, 2021
INVENTOR(S) : Alon Baram et al.

It is certified that error appears in the above-identified patent and that said Letters Patent is hereby corrected as shown below:

In the Specification

In Column 1, Line 41, delete "at 30" and insert -- workstation 12 --, therefor.
In Column 6, Line 52, delete "((X,re),"  and insert -- (X,re), --, therefor.
In Column 8, Line 3, delete "re," and insert -- re). --, therefor.
In Column 8, Line 55, delete "1.4=3." and insert -- 1.4mm3. --, therefor.

Signed and Sealed this
Eighth Day of November, 2022

Katherine Kelly Vidal
*Director of the United States Patent and Trademark Office*